Jan. 22, 1974 B. J. MACHIN Plant Pat. 3,447
CHRYSANTHEMUM PLANT
Filed Dec. 27, 1971
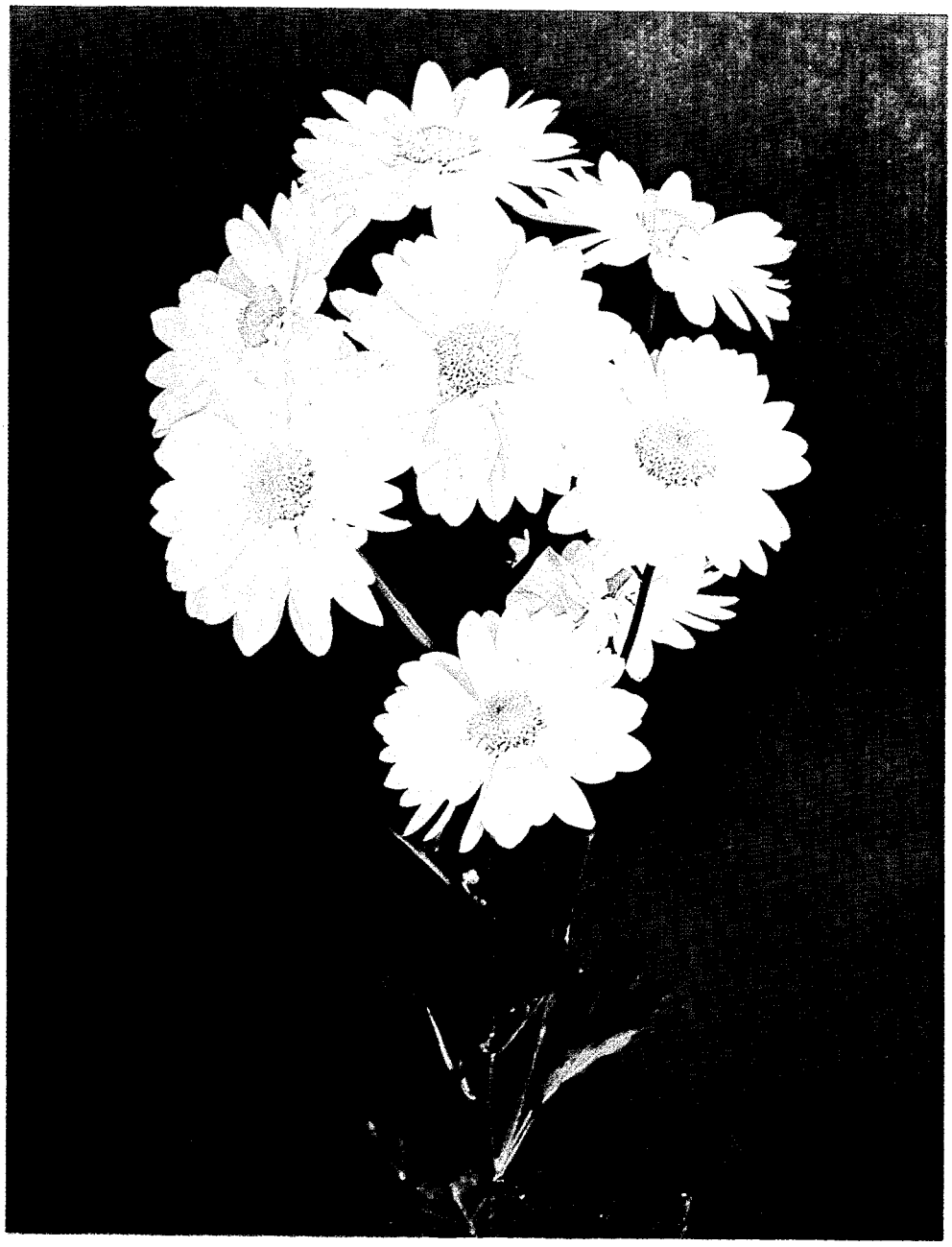

United States Patent Office

Plant Pat. 3,447
Patented Jan. 22, 1974

3,447

CHRYSANTHEMUM PLANT

Barrie John Machin, East Broyle Estate, Chichester, England, assignor to Frampton's Nurseries Limited, Chichester, Sussex, England

Filed Dec. 27, 1971, Ser. No. 212,831
Int. Cl. A01h *5/00*
U.S. Cl. Plt.—74 1 Claim

This invention relates to a new and distinct variety of *Chrysanthemum morifolium* Bailey (spray type) known as Nina. Nina is a seedling originated by me from a cross made in 1967 between the unpatented variety Coronado and the unpatented variety Pink Marble, the former being the seed parent, and the latter being the pollen parent.

The variety Nina resulted from an extensive breeding program with the object of producing improved varieties for year round chrysanthemum production programs with more vigor and reduced flowering time compared with existing varieties. The immediate objective was to produce a white spray more vigorous and more responsive than Bonnie Jean, but without the foliage problems of White Marble:

Nina has the improved characteristics over the related variety White Marble:

(1) It has no foliage problems in various environmental conditions.
(2) It has a 9 week flowering response.

Nina has the following improved characteristics over the related variety Bonnie Jean:

(1) Its color is pure white as compared with creamy white.
(2) It responds in 9 weeks of short days instead of 10 or 11 weeks of short days.
(3) It is more vigorous and will produce a longer stem under similar longday conditions.

As compared with its seed parent, Nina has a more uniform habit of growth and is more easily controllable in year round programs in Europe. It also has a more vigorous habit and stronger stems.

As compared with the white sport of its pollen parent, Nina does not suffer from chlorotic foliage in any known soil conditions and has shorter internodes.

Assexual reproduction of this new variety Nina by rooting vegetative shoots in Sussex, England, shows that the above characteristics are fixed and come true to type through succeeding generations.

The accompanying drawing shows a typical flower of my new variety depicted in color as nearly true as it is reasonably possible to make the same in color illustration of this character.

The following is a detailed description of the new variety Nina, with color terminology in accordance with the Royal Horticultural Society color chart, hereinafter referred to as RHS.

Genus: Chrysanthemum
Species: *Morifolium* Bailey
Type: Spray
Class: Single
Breeding: The original seedling resulted from a cross between the variety Coronado, the seed parent, and Pink Marble, the pollen parent. The cross was made in 1967 at Frampton's Nurseries Ltd., Forbridge Nursery, Chichester, Sussex, England.
Propagation: Holds its distinguishing characteristics through succeeding propagations by rooting vegetative shoots.
Flower: When grown and observed in Sussex, England, 6 to 12 flowers are borne on pedicels after removal of the main apical bud.
Bloom:
*Size.*—Average diameter is 9 cm. when fully open.
*Petalage.*—Single, approximately 40 ray petals. Diameter of disc is 2 cm.
*Form.*—Single, with slightly reflexing petals.
*Petals.*—Long, broad, overlapping, blunt, flat and of medium texture.
Pedicels: Wiry and 8 cm. in length.
Color of open bloom:
Inner face of fully expanded petal, RHS 155D.
Outer face of fully expanded petal, RHS 155D.
Inner face of yound petal, RHS 155D.
Outer face of young petal, RHS 155D.
Response Group: 9 weeks.
Temperature tolerance: 55–60° F. at night.
Plant: Strong upright habit of growth, medium vigor.
Foliage:
Good quality; average internode length, 2½ cm.; medium size.
Color, RHS 143C.
Texture, medium.
Stem:
Medium thickness, and strong.
Color 144B at flowering.
Water uptake, good.

I claim:

1. A new and distinct variety of *Chrysanthemum morifolium* Bailey, spray type, substantially as herein shown and described, characterized particularly as to novelty by the unique combination of a nine week flowering response during short days, a uniform habit of growth, and the ability to maintain the normal green color of its foliage under a wide variety of soil conditions.

No references cited.

ROBERT E. BAGWILL, Primary Examiner